United States Patent
Yamada et al.

(10) Patent No.: US 7,939,289 B2
(45) Date of Patent: May 10, 2011

(54) DISTINCTION METHOD FOR THE CATCH CAPACITY OF PROTEINS

(75) Inventors: Akira Yamada, Koganei (JP); Kazuhiro Oiwa, Koganei (JP)

(73) Assignee: National Institute of Information and Communications Technology, Tokyo (JP)

( * ) Notice: Subject to any disclaimer, the term of this patent is extended or adjusted under 35 U.S.C. 154(b) by 1688 days.

(21) Appl. No.: 11/186,026

(22) Filed: Jul. 21, 2005

(65) Prior Publication Data

US 2006/0105463 A1    May 18, 2006

(30) Foreign Application Priority Data

Nov. 15, 2004  (JP) ................ P2004-331158

(51) Int. Cl.
 *C12Q 1/25*    (2006.01)
 *C07K 14/00*   (2006.01)
(52) U.S. Cl. ................. 435/21; 530/350; 514/2
(58) Field of Classification Search .......... None
 See application file for complete search history.

(56) References Cited

FOREIGN PATENT DOCUMENTS

JP    2004-109695    8/2004

OTHER PUBLICATIONS

Yamada et al.,"An in vitro assay reveals essential protein components for the "catch" state of invertebrate smooth muscle", PNAS 98(12): 6635-6640 (Jun. 2001).*
Approach Mechanism Where the Adductor Muscle of a Bivalve Controls Energy Consumption and Enables Maintenance of A Closed Shell; The Heredity, Sep. 2001, vol. 55, No. 5.
Akira Yamada et al., An In Vitro Assay Reveals Essential Protein Components for the "Catch" State Of Invertebrate Smooth Muscle; PNAS, Jun. 5, 2001, vol. 98, No. 12, 6635-6640.
Yasutaka Tsutsui et al., In Vitro Reconstitution of the Catch State Using Myofilaments From Bivalve Obliquely Striated Muscle; Zoological Science, 2003, vol. 20, No. 12, p. 1539.

* cited by examiner

*Primary Examiner* — Anand U Desai

(57) ABSTRACT

A distinction method is provided to distinguish catch capacity where myosin, a protein that constitutes muscles, or filaments containing myosin bind to actin due to the contribution of twitchin that constitutes thick filaments along with myosin, while certain tension is sustained. The catch capacity is distinguished by using synthetic thick filaments containing myosin and twitchin, which are obtained from an extract of the muscles with a predetermined high salt buffer solution, and a soluble protein fraction obtained from the suspension of the above-mentioned muscles.

8 Claims, 7 Drawing Sheets

US 7,939,289 B2

DISTINCTION METHOD FOR THE CATCH CAPACITY OF PROTEINS

BACKGROUND OF THE INVENTION

1. Field of the Invention

The present invention relates to a distinction method of the 'catch' capacity of proteins for the purpose of distinguishing whether proteins that constitute muscles can form the catch state.

2. Description of Related Art

Conventionally, in the muscles of shellfish, other than in an active state where actin, which is a protein component of muscles, is moved by myosin causing the contraction of the muscles, and in a relaxed state, where myosin or filaments containing myosin do not interact with actin, the muscles become relaxed, it has been known that a state is formed referred to as a 'catch' state in which myosin or filaments containing myosin bind to actin while high tension is sustained at low energy consumption (Rüegg, 1971; Watabe and Hartshorne, 1990).

SUMMARY OF THE INVENTION

The inventors of the present invention have succeeded in reconstituting the above-mentioned catch state and relaxed state in vitro using protein filaments prepared from muscles or proteins purified from muscles (Proceedings of National Academy of Sciences, Jun. 5, 2001, Vol. 98; pp 6635-6640 and Genetics, September, 2001), and also expect to develop a totally new device, which can be used in a nanomachine, by utilizing the mechanisms of the catch and relaxed states.

Therefore, it has an extremely important meaning to check whether or not muscles, or tissues other than muscles can form the catch state, or how easily the catch state can be formed.

Conventionally, these are checked using a method where actin, myosin and twitchin, which constitutes thick filaments along with myosin and relates to the catch state, are purified from the muscles, the catch state being detected using these purified proteins, or another method where the catch state is detected using native thin filaments containing actin and native thick filaments containing myosin and twitchin obtained from muscles.

However, there is a problem with protein purification method, because it requires a complicated operation, and takes time to purify the protein.

In the meantime, with a method using native filaments, since the native thick filament fraction contains actin and contains large amount of paramyosin which does not contribute to the catch state, it has been known that approximately one-half of the thick filaments do not bind to actin filaments. In other words, the sensitivity is considerably low compared to the case of using purified proteins. In addition, since native thick filaments are heterogeneous, there is the problem that it is difficult to obtain accurate data concerning the binding and dissociation of actin to myosin or filaments containing myosin.

Then, in order to resolve these problems in one stroke, a useful distinction method is provided for a catch capacity of proteins where the operation is simple; the data is accurate; and the detection sensitivity is high.

In other words, the present invention is a distinction method for catch capacity, i.e. the capacity to form the catch state where actin and myosin, proteins that constitute muscles, or filaments containing myosin bind to each other due to the contribution of twitchin comprising thick filaments along with myosin, while certain tension is sustained, and is a distinction method for a catch capacity designed to distinguish the catch capacity of proteins using synthetic thick filaments containing myosin and twitchin prepared from muscle extracts with a predetermined high salt buffer solution. Here, "myosin or filaments containing myosin" indicate the state of myosin that constitutes filaments, myosin that does not constitute filaments, or myosin that constitutes filaments containing twitchin or other protein.

Another embodiment of the present invention is a catch capacity distinction method that distinguishes whether myosin, a protein that constitutes muscles, or filaments containing myosin bind to actin due to the contribution of twitchin comprising thick filaments along with myosin, while a certain tension is sustained, and is a distinction method for a catch capacity designed to distinguish the catch capacity of proteins using synthetic thick filaments containing myosin and twitchin prepared from extracts of the above-mentioned muscles with a predetermined high salt buffer solution. Concurrently, use can be made of a soluble protein fraction containing enzymes and some other substances that activate them that initiate the catch state, obtained from the muscles.

In this case, if it is designed to obtain the above-mentioned extracts obtained using the high salt buffer solution from the precipitate after the extraction of the soluble protein fraction, because the synthetic thick filaments and the soluble protein fraction required for the reconstitution of the catch state can be simultaneously efficiently obtained, an experiment to distinguish the catch capacity can be efficiently conducted without waste.

According to the present invention, compared to a complicated operation to purify myosin and twitchin from muscles, the catch capacity can be distinguished using the synthetic thick filaments obtained by an extremely simple fractionation operation to distinguish whether or not the catch capacity is retained, or how much catch capacity is retained as in the prior art.

In addition, this synthetic thick filament fraction contains little actin, and the content of paramyosin, which does not contribute to the formation of the catch state, is lower than that of the native thick filaments, so detection sensitivity is higher, enabling accurate data acquisition.

In other words, a distinction method for the catch capacity of muscles where the operation is simple; detection sensitivity is high; and accurate data can be obtained can be provided.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
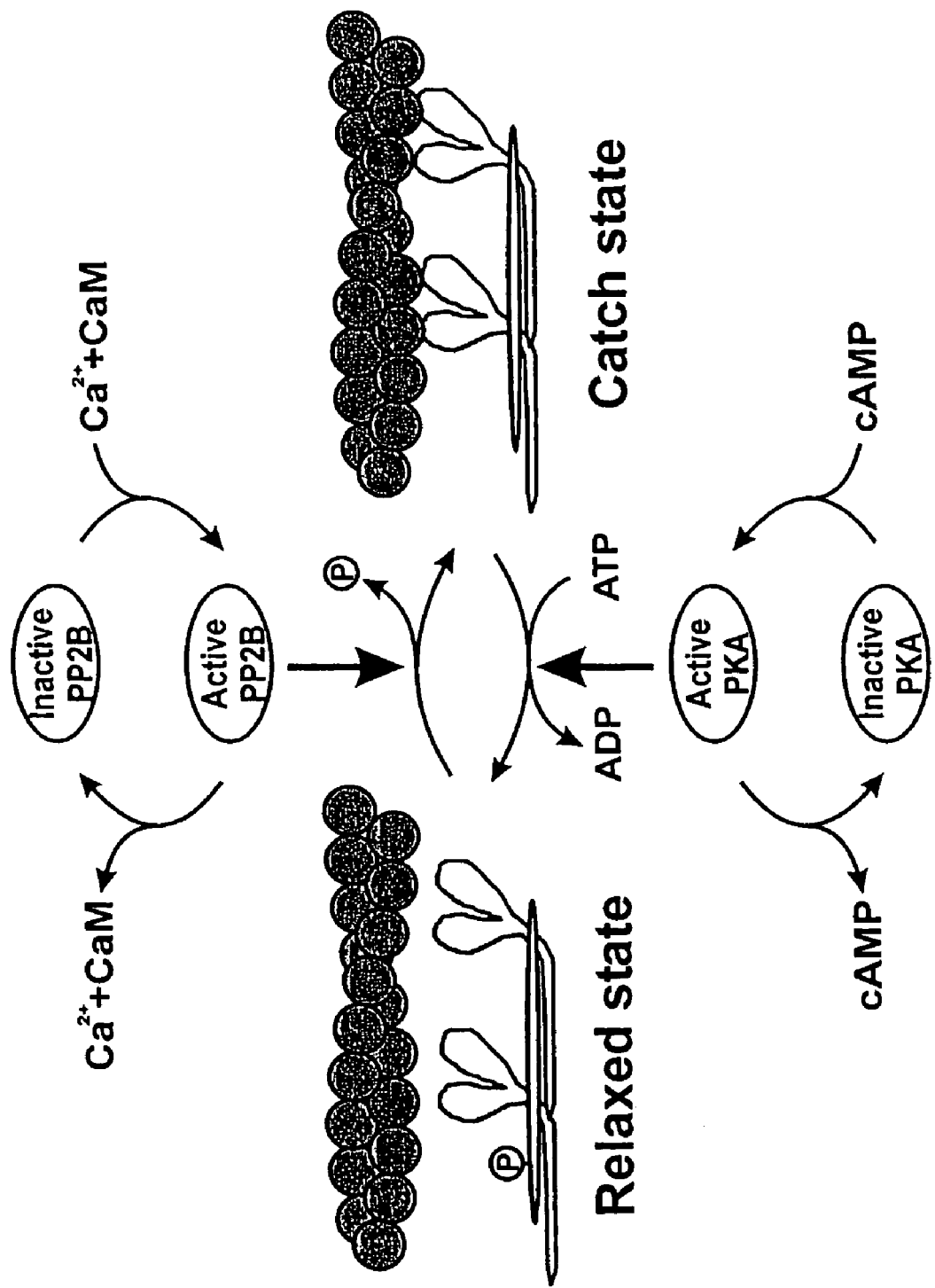
FIG. 1 shows a schematic outline explanatory diagram disclosing the catch and relax state of twitchin.

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

This distinction method for the catch capacity is a method to distinguish the catch capacity, capable of initiating a catch state where myosin, a protein component of muscles, or filaments containing myosin bind to actin due to the contribution of twitchin that constitutes the thick filaments along with myosin, while a certain tension is sustained, and it is a distinction method for the catch capacity designed to distinguish the catch capacity of proteins using synthetic thick filaments containing myosin and twitchin, which are obtained from muscle extracts with a predetermined high salt buffer solution, and using a soluble protein fraction obtained from the above-mentioned muscles.

Further, the distinction method for the catch capacity in the present embodiment was applied to the byssus retractor muscles and the posterior adductor muscle (smooth muscles) of *M. galloprovincialis*, which obviously have the catch capacity.

As for actin, actin filaments purified from rabbit skeletal muscles were used. These were labeled with tetramethylrhodamine phalloidin (Sigma, P-1951), and adjusted to a final concentration of 2 μg/ml. Actin does not have to be extracted from muscles to be distinguished whether or not the catch capacity is retained.

The synthetic thick filaments were prepared from the above-mentioned byssus retractor muscles and the posterior adductor muscle of *M. galloprovincialis*. These muscles were first homogenized in a predetermined buffer and the soluble protein fraction, which will be described later, was extracted. The precipitate was further extracted with a high salt buffer solution and the synthetic thick filaments were obtained from this extract by dialysis.

Specifically, a buffer solution where the above-mentioned muscles of *M. galloprovincialis* were suspended for the extraction of the soluble protein fraction, in the present embodiment, contained 80 mM NaCl, 2 mM $MgCl_2$, 0.5 mM EGTA, 2 mM dithiothreitol (hereafter, referred to as DTT) and 20 mM Pipes-NaOH, and was adjusted to be pH 7.0.

The above-mentioned suspension was centrifuged (for example, at 300,000×g for 30 min.), and its precipitate, where the supernatant had been removed, was extracted with a high salt buffer solution. As this high salt buffer solution, in the present embodiment, 10 mM phosphate buffer containing 0.4 M KCl, 4 mM $MgCl_2$, 4 mM ATP, 4 mM EGTA and 2 mM DTT adjusted to be pH 7.0 was used. After the centrifugation (for example, at 300,000×g for 30 min.), five volumes of cold water was added to the supernatant, and was further centrifuged. The precipitate was then dissolved in the above-mentioned phosphate buffer, and the solution was dialyzed against the buffer used for the extraction of the soluble protein fraction, without stirring.

For the soluble protein fraction containing enzymes for the purpose of reconstituting the catch state, the above-mentioned suspension was centrifuged (for example, at 300,000×g for 30 min.), and the obtained supernatant was used.

The procedure for distinguishing the catch capacity of muscles using the above-mentioned synthetic thick filaments and soluble protein fraction is explained as follows.

In the present embodiment, not only the reconstitution of the catch state but also the reconstitution of the relaxed state, in which actin do not bind to myosin filaments, was also observed. Furthermore, the relaxed state and the catch state are reversibly exchangeable. Concerning these mechanisms, the inventors have clarified that twitchin is dephosphorylated by serine/threonine protein phosphatase 2B (referred to as 'PP2B' in the diagram), a protein dephosphorylation enzyme in muscles, and the state is converted to the catch state as shown in FIG. 1. Further, it is already clear that twitchin is phosphorylated by protein kinase A (referred to as 'PKA' in the diagram), a protein phosphorylation enzyme in muscles, and that the state is converted to the relaxed state, as well.

The binding of actin to the synthetic thick filaments was observed using a dark field microscope and a fluorescence microscope, as shown in FIGS. 2 through 5.

Figure 2:
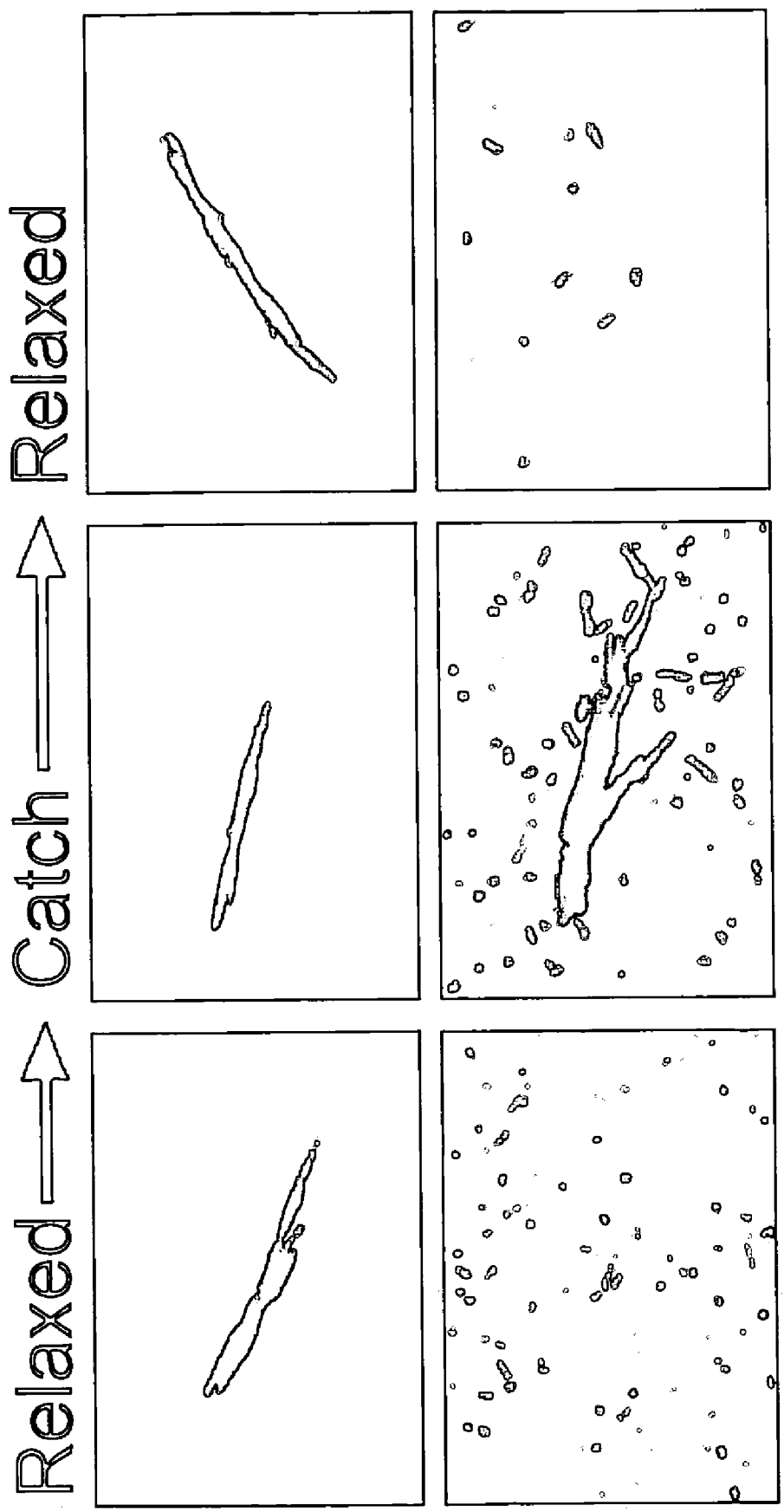
FIG. 2 shows pictures representing the state of protein for the explanation of FIG. 1.
Figure 4:
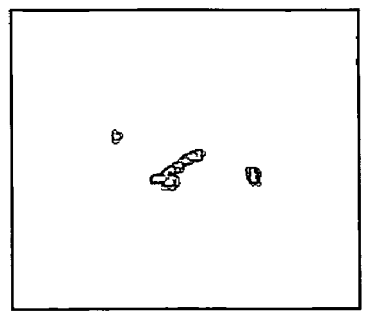
FIG. 4 shows pictures representing the state of the protein obtained in said embodiment.
Figure 3:
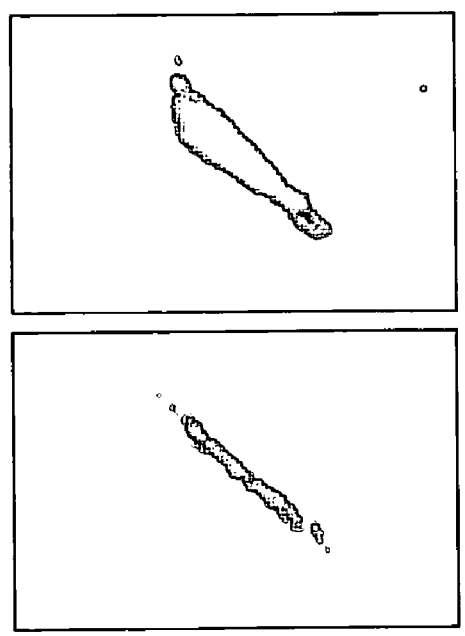
FIG. 3 shows pictures representing the state of the protein obtained in one embodiment of the present invention.
Figure 5:
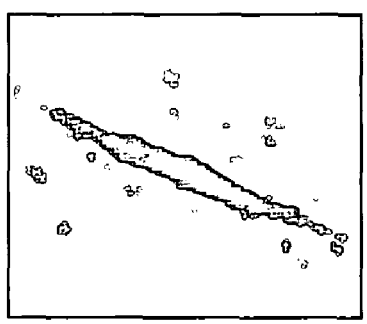
FIG. 5 shows pictures representing the state of the protein obtained in said embodiment.
Figure 5:
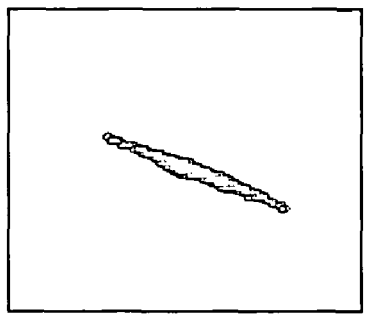

In the pictures, the filaments observed with a dark field microscope were synthetic thick filaments, and as shown in the upper pictures of FIG. 2 and in the left pictures in FIGS. 3 through 5, they were observed as bundles of long filaments. The filaments observed with a fluorescence microscope were fluorescence-labeled actin filaments as described below, and as shown in the lower pictures of FIG. 2 and the right pictures of FIGS. 3 through 5.

First, the synthetic thick filaments ($2^{-3}$ μg/ml) and the soluble protein fraction (approximately 0.1 mg/ml) were mixed in the presence of $10^{-5}$ M $Ca^{2+}$, in what is referred to as a 'catch treatment'. When the synthetic thick filaments, where the catch treatment had been performed, and actin filaments were mixed in the presence of MgATP at a low free $Ca^{2+}$ concentration ($10^{-7}$ M or lower), as shown in FIG. 3, it was clear that the catch state in which binding of actin filaments to the synthetic thick filaments were observed was formed; in other words, the muscles had the catch capacity.

Further, the synthetic thick filaments and the soluble protein fraction were mixed in the presence of $10^{-5}$ M cAMP and $1^{-4}$ mM ATP. This is referred to as a 'relaxation treatment'. When the synthetic thick filaments, where the relaxation treatment had been performed, and actin filaments were mixed in the presence of MgATP at a low free $Ca^{2+}$ concentration ($10^{-7}$ M or lower), as shown in FIG. 4, the binding of the actin filaments to the synthetic thick filaments was no longer observed, and the relaxed state was formed.

When the catch treatment was further performed again using the soluble protein fraction, and the resultant synthetic thick filaments were mixed with actin filaments, the state returns to the catch state as shown in FIG. 5.

Figure 6:
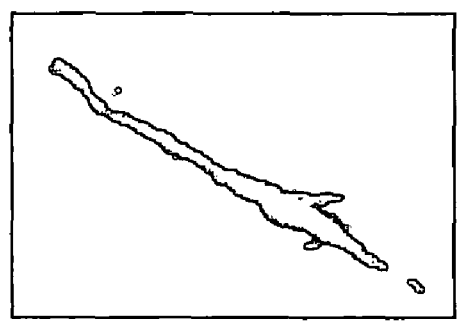
FIG. 6 shows pictures representing the state of the protein obtained in said embodiment.
Figure 6:
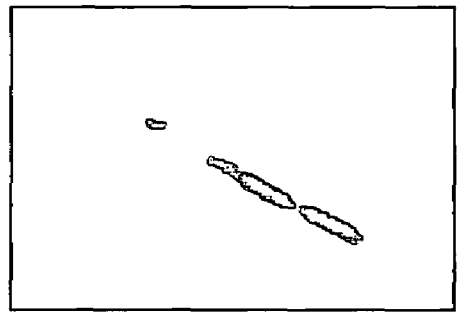
Figure 8:
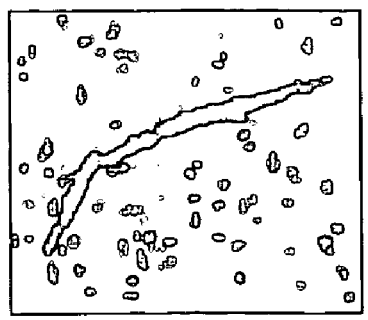
FIG. 8 shows pictures representing the state of the protein obtained in said embodiment.
Figure 8:
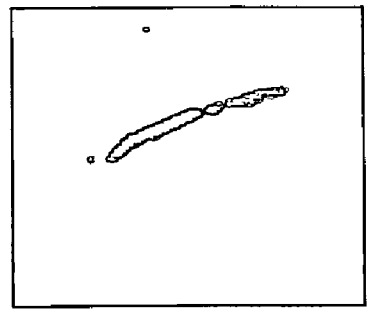
Figure 7:
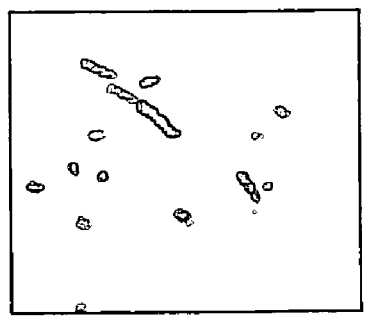
FIG. 7 shows pictures representing the state of the protein obtained in said embodiment.
Figure 7:
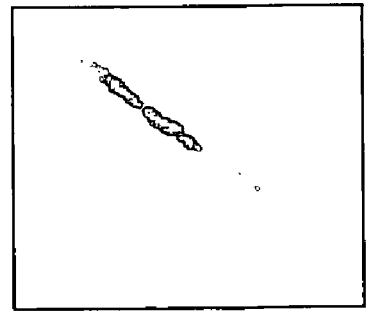

The observation pictures obtained where the catch capacity was distinguished using the synthetic thick filaments as described above were compared to those where using the purified myosin filaments and twitchin shown in FIGS. 6 through 8. Viewing the fluorescent pictures where actin filaments bound to the thick filaments were observed, almost the same amount of actin filaments bound to the synthetic thick filaments as that bound to the purified myosin filaments. In other words, it is clear that the detection sensitivity was almost the same as that when purified proteins were used.

Figure 9:
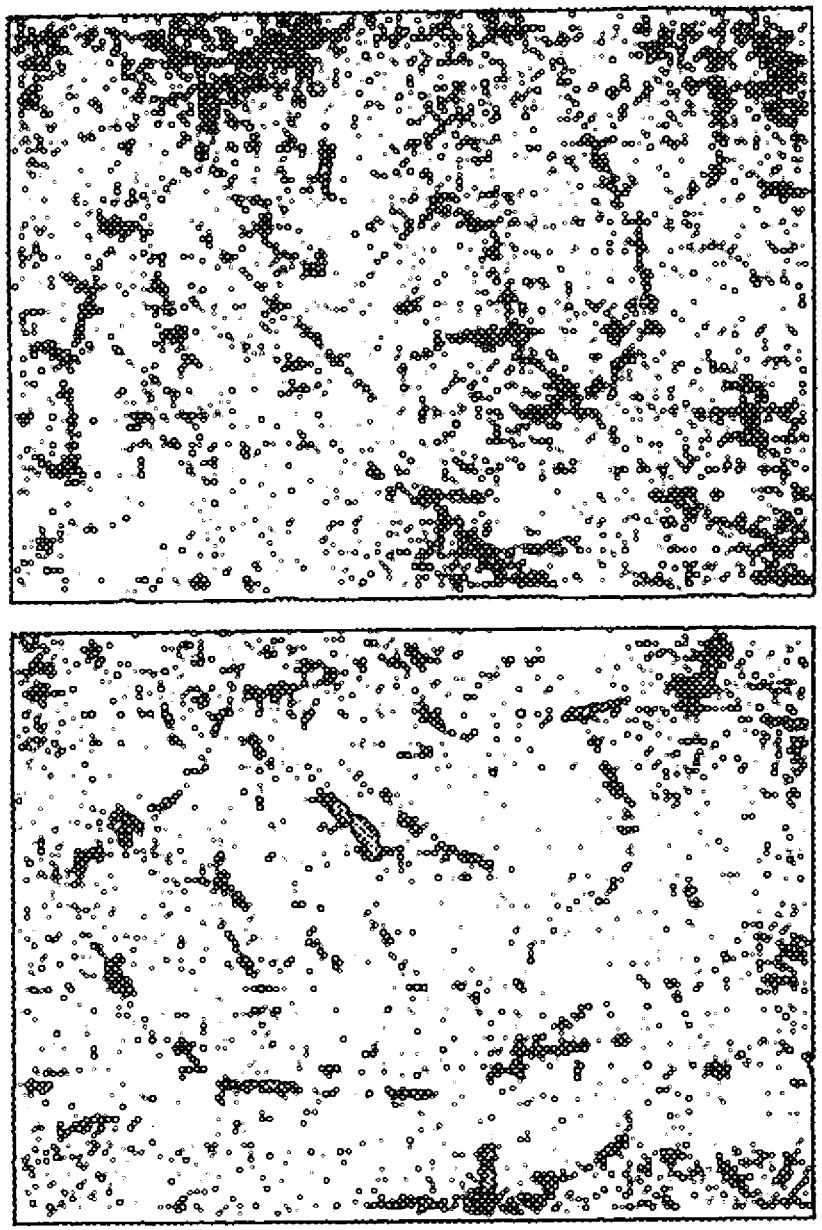
FIG. 9 shows pictures representing the state in the case of using native filaments.

In the meantime, a comparison of the synthetic filaments to the native filaments, as shown in FIG. 9, a picture (upper picture) of the native thick filaments containing myosin and twitchin observed with a dark field microscope and another picture (lower picture) of the native thin filaments containing actin observed with a fluorescence microscope are not very clear. In other words, it is difficult to obtain clear data by using native filaments.

Figure 10:
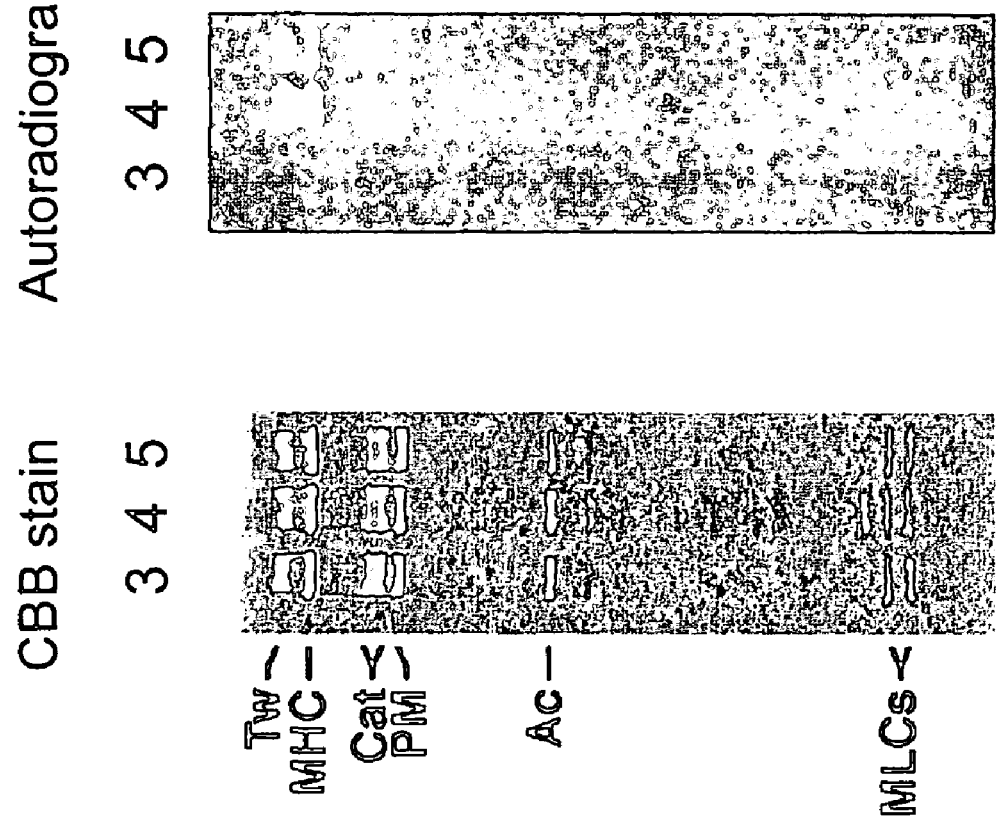
FIG. 10 shows views representing results of an SDS-PAGE and autoradiography of synthetic thick filaments according to said embodiment.

The synthetic thick filaments were analyzed by an SDS-PAGE and autoradiography using $[\gamma^{-32}P]$ ATP, and the results are shown in FIG. 10. In the pictures, filaments marked 3, 4 and 5 respectively indicate synthetic thick filaments after the catch treatment, those where the relaxation treatment was further performed in the presence of $[\gamma^{-32}P]$ ATP, and those where further catch treatment was performed.

As is obvious from the results of the SDS-PAGE shown in FIG. 10, only a minute amount of actin (referred to as 'Ac' in the picture) was contained. Further, the content of paramyosin that does not contribute to the catch state (referred to as 'PM' in the picture) was almost the same or slightly less compared to that of the myosin heavy chain (referred to as 'MHC' in the picture). These greatly differed from the native thick filament fraction in that it contains a considerable amount of actin and more paramyosin than myosin.

According to the distinction method for the catch capacity of muscles in the above described embodiment, compared to the conventional method in which purified myosin and twitchin are used, the procedure is much simpler, and the detection sensitivity is almost the same.

Further, the synthetic thick filament preparation according to the present embodiment contains less actin, which is an obstacle to observing the catch state, than the native thick filament fraction, and the content of paramyosin which does not contribute to the formation of the catch state, is smaller, so the detection sensitivity is higher and more accurate data can be obtained.

Furthermore, the present invention is not limited to the present embodiment.

In the above-mentioned embodiment, the soluble protein fraction extracted from the same muscle from which the synthetic thick filaments were prepared was used as enzymes for the purpose of initiating and terminating the catch state. However, for example, if it is difficult to fractionate the soluble protein fraction or if the soluble protein is unstable, a purified product of calcineurin (for example, bovine calcineurin), which, the inventors have clarified, is an enzyme initiating the catch state, and which is one of serine/threonine protein phosphatase 2B, and calmodulin which activates calcineurin can be used for the initiation of the catch state.

An explanation is provided hereafter of an experiment to reconstitute the catch state and the relaxed state using the above-mentioned actin filaments, synthetic thick filaments, bovine calcineurin, and bovine protein kinase A (hereafter, referred to as 'PKA') which is an enzyme to form the above-mentioned relaxed state.

In the presence of $10^{-5}$ M cAMP and $1^{-4}$ μM ATP, 2 μg/ml of bovine PKA (Sigma P-5511) is added to the synthetic thick filaments in the catch state shown in FIG. 3, and the relaxed state is formed.

In the meantime, 0.2 μM bovine calcineurin (Sigma C-1907) and 2 μM calmodulin (Sigma P-2277) are added to the synthetic thick filaments in the relaxed state in the presence of $10^{-5}$ M free $Ca^{2+}$. After incubation at room temperature (24° C.) for 10 min, excess EGTA is added to lower the free $Ca^{2+}$ concentration to $10^{-7}$ M or less. After this process, actin filaments again bound to the synthetic thick filaments. In other words, it is clear that the synthetic thick filaments in the above-mentioned embodiment are sufficiently useful in an assay system for distinguishing the catch capacity of muscles not only using the soluble protein fraction but also using purified enzymes.

The specific configuration of each section is also not limited to that of above-mentioned embodiment, but is variously modifiable within the scope of the purpose of the present invention.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A method for determining catch capacity of proteins from a tissue sample for the purpose of distinguishing the capacity of initiating the catch state where myosin, a protein that constitutes muscles, or filaments containing myosin bind to actin due to the contribution of twitchin that constitutes thick filaments along with myosin, while a certain tension is sustained, the method for the catch capacity of proteins designed to distinguish the catch capacity comprising the steps of:
   preparing synthetic thick filaments containing myosin and twitchin from the extract of said muscles from the tissue sample with a high salt buffer solution which has a salt concentration equal to the concentration of 10 mM phosphate buffer containing 0.4 M KCl, 4 mM $MgCl_2$, 4 mM ATP, 4 mM EGTA and 2 mM DTT adjusted to be pH 7.0 by fractionation operation;
   mixing the synthetic thick filament and actin filaments;
   performing a catch treatment on the synthetic thick filaments; and
   determining the catch capacity of the proteins by detecting the binding of actin filaments to the synthetic thick filaments.

2. The method of claim 1 wherein the synthetic thick filaments were prepared from a precipitate of a suspension obtained by homogenizing the tissue sample with centrifugal processing.

3. The method of claim 2 further comprising the step of:
   preparing soluble protein fraction as a supernatant of a suspension obtained by homogenizing the tissue sample with centrifugal processing, and wherein
   the catch treatment is performed by mixing the synthetic thick filaments and the soluble protein fraction.

4. The method of claim 1 wherein
the synthetic thick filaments comprise paramyosin.

5. The method of claim 1 wherein,
the synthetic thick filaments comprise paramyosin and actin wherein,
the contents of paramyosin and actin are lower than those of native thick filament fraction.

6. The method of claim 1 wherein,
the synthetic thick filaments consist essentially of twitchin, myosin heavy chain, catchin, paramyosin, actin and myosin light chain wherein,
the contents of paramyosin and actin are lower than those of native thick filament fraction.

7. A method for determining a catch capacity of proteins from a tissue sample comprising the steps of:
preparing synthetic thick filaments comprising paramyosin from the tissue sample;
mixing the synthetic thick filaments and actin filaments;
performing a catch treatment on the synthetic thick filaments; and
determining the catch capacity of the proteins by detecting the binding of actin filaments to the synthetic thick filaments,
the synthetic thick filaments comprise paramyosin and actin wherein,
the contents of paramyosin and actin are lower than those of native thick filament fraction.

8. A method for determining a catch capacity of proteins from a tissue sample comprising the steps of:
preparing synthetic thick filaments comprising paramyosin from the tissue sample;
mixing the synthetic thick filaments and actin filaments;
performing a catch treatment on the synthetic thick filaments; and
determining the catch capacity of the proteins by detecting the binding of actin filaments to the synthetic thick filaments,
the synthetic thick filaments consist essentially of twitchin, myosin heavy chain, catchin, paramyosin, actin and myosin light chain wherein
the contents of paramyosin and actin are lower than those of native thick filament fraction.

* * * * *